United States Patent
Luckemeyer et al.

(10) Patent No.: US 12,403,239 B2
(45) Date of Patent: Sep. 2, 2025

(54) DISPOSABLE CARTRIDGE FOR VACUUM ACTUATED FLUID DELIVERY

(71) Applicant: Solventum Intellectual Properties Company, Maplewood, MN (US)

(72) Inventors: James A. Luckemeyer, San Antonio, TX (US); Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 32 days.

(21) Appl. No.: 18/538,759

(22) Filed: Dec. 13, 2023

(65) Prior Publication Data
US 2024/0115797 A1   Apr. 11, 2024

Related U.S. Application Data

(62) Division of application No. 16/432,206, filed on Jun. 5, 2019, now Pat. No. 11,890,437, which is a division
(Continued)

(51) Int. Cl.
*A61M 3/02* (2006.01)
*A61F 13/05* (2024.01)
(Continued)

(52) U.S. Cl.
CPC .......... *A61M 3/0254* (2013.01); *A61M 1/743* (2021.05); *A61M 1/92* (2021.05);
(Continued)

(58) Field of Classification Search
CPC ............... A61F 13/00017; A61F 13/05; A61B 17/3205; A61B 17/32; B65D 83/0077;
(Continued)

(56) References Cited

U.S. PATENT DOCUMENTS 1,355,846 A   10/1920   Rannells
2,547,758 A    4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Nicholas J. Weiss
*Assistant Examiner* — Gabriella E Burnette (57) ABSTRACT

Systems, methods, and apparatuses for providing instillation therapy with a negative-pressure source are described. The apparatus can include a housing having a dosing chamber and a negative-pressure chamber fluidly isolated from each other. The apparatus can also include a moveable barrier disposed in the housing between the dosing chamber and the negative-pressure chamber. The housing includes a fluid inlet in fluid communication with the dosing chamber and a fluid outlet in fluid communication with the dosing chamber. The housing can also include a negative-pressure inlet in fluid communication with the negative-pressure chamber and a biasing element coupled to the moveable barrier. The biasing element is operable to move the moveable barrier between a charge position and a discharge position.

7 Claims, 5 Drawing Sheets

Related U.S. Application Data of application No. 14/794,269, filed on Jul. 8, 2015, now Pat. No. 10,350,336.

(60) Provisional application No. 62/026,500, filed on Jul. 18, 2014.

(51) Int. Cl.
  *A61M 1/00* (2006.01)
  *A61M 5/142* (2006.01)
  *A61M 5/145* (2006.01)
  *A61M 5/168* (2006.01)

(52) U.S. Cl.
  CPC ............ *A61M 1/94* (2021.05); *A61M 3/0208* (2014.02); *A61M 3/022* (2014.02); *A61M 5/14224* (2013.01); *A61M 5/16881* (2013.01); *A61F 13/05* (2024.01); *A61M 3/0201* (2021.05); *A61M 3/0241* (2013.01); *A61M 2005/14506* (2013.01); *A61M 2205/12* (2013.01); *A61M 2205/128* (2013.01); *A61M 2205/3334* (2013.01); *A61M 2205/3337* (2013.01); *A61M 2205/50* (2013.01)

(58) Field of Classification Search
  CPC . B65D 83/0038; A61M 3/0254; A61M 1/743; A61M 1/92; A61M 1/94; A61M 3/0208; A61M 3/022; A61M 5/14224; A61M 5/16881; A61M 3/0201; A61M 3/0241; A61M 2005/14506; A61M 2205/12; A61M 2205/128; A61M 2205/3334; A61M 2205/3337; A61M 2205/50; A61M 1/72; A61M 1/96; A61M 5/16813; A61M 2205/14; A61M 2205/3331; A61M 39/227; A61M 39/281; F16K 7/07
  See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,932,065 A * | 1/1976 | Ginsberg | G01F 11/021 417/399 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,542,918 A * | 8/1996 | Atkinson | A61M 3/0254 604/35 |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,836,909 A * | 11/1998 | Cosmescu | A61M 1/743 604/35 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,611,500 B1 * | 11/2009 | Lina | A61M 1/75 604/304 |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |

(56) References Cited

U.S. PATENT DOCUMENTS

| | | | |
|---|---|---|---|
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2009/0213519 | A1* | 8/2009 | Bedingfield .......... H01F 7/1844 361/160 |
| 2013/0085462 | A1* | 4/2013 | Nip ...................... A61M 1/962 604/315 |
| 2013/0177455 | A1* | 7/2013 | Kamen ................. G16H 20/17 417/313 |
| 2013/0211318 | A1* | 8/2013 | Croizat .................. A61M 1/77 604/23 |
| 2014/0163491 | A1 | 6/2014 | Schuessler et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713, Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

DISPOSABLE CARTRIDGE FOR VACUUM ACTUATED FLUID DELIVERY

This application is a divisional of U.S. patent application Ser. No. 16/432,206, filed Jun. 5, 2019, entitled "Disposable Cartridge for Vacuum Actuated. Fluid Delivery," which is a divisional of U.S. patent application Ser. No. 14/794,269, filed Jul. 8, 2015, entitled "Disposable Cartridge for Vacuum Actuated Fluid Delivery," which claims the benefit under 35 USC § 119(e), of the filing of U.S. Provisional Patent Application No. 62/026,500, entitled "Disposable Cartridge for Vacuum Actuated Fluid Delivery," filed Jul. 18, 2014, which is incorporated herein by reference for all purposes.

TECHNICAL FIELD

The invention set forth in the appended claims relates generally to tissue treatment systems and more particularly, but without limitation, to a disposable cartridge for providing instillation therapy with a negative-pressure source.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

In addition, the delivery of therapeutic fluids (e.g. saline or antibiotic fluids) to the tissue site can also provide benefits to healing of a tissue site. Treatment of tissue sites with the delivery of therapeutic fluids may also be referred to as "instillation therapy." Instillation therapy may assist in cleaning the tissue site by aiding in the removal of infectious agents or necrotic tissue. The therapeutic fluids used in instillation therapy may also provide medicinal fluids, such as antibiotics, anti-fungals, antiseptics, analgesics, or other similar substances, to aid in the treatment of a tissue site.

While the clinical benefits of negative-pressure therapy and instillation therapy are widely known, the cost and complexity of negative-pressure therapy and instillation therapy can be a limiting factor in its application, and the development and operation of delivery systems, components, and processes continues to present significant challenges to manufacturers, healthcare providers, and patients.

BRIEF SUMMARY

New and useful systems, apparatuses, and methods for providing instillation therapy in a negative-pressure therapy environment are set forth in the appended claims. Illustrative embodiments are also provided to enable a person skilled in the art to make and use the claimed subject matter. For example, an apparatus for providing instillation therapy with a negative-pressure source is described. The apparatus may include a housing having a dosing chamber and a negative-pressure chamber fluidly isolated from each other. The apparatus may also have a moveable barrier disposed in the housing between the dosing chamber and the negative-pressure chamber. A fluid inlet may be in fluid communication with the dosing chamber, and a fluid outlet may be in fluid communication with the dosing chamber. A negative-pressure inlet may also be in fluid communication with the negative-pressure chamber. The apparatus can also include a biasing element coupled to the moveable barrier and operable to move the moveable barrier between a charge position and a discharge position.

In other embodiments, a therapy system for providing instillation therapy and negative-pressure therapy is described. The system can include a negative-pressure source, a fluid source, and a cartridge. The cartridge may include a housing having a dosing chamber and a negative-pressure chamber fluidly isolated from each other. The cartridge may also have a moveable barrier disposed in the housing between the dosing chamber and the negative-pressure chamber. A fluid inlet may be in fluid communication with the dosing chamber, and a fluid outlet may be in fluid communication with the dosing chamber. A negative-pressure inlet may also be in fluid communication with the negative-pressure chamber. The cartridge can also include a biasing element coupled to the moveable barrier and operable to move the moveable barrier between a charge position and a discharge position.

In still other embodiments, a method for providing instillation therapy with a negative-pressure source is described. A negative-pressure source, a fluid source, and a cartridge may be provided. The cartridge may include a housing having a dosing chamber and a negative-pressure chamber fluidly isolated from each other. The cartridge may also have a moveable barrier disposed in the housing between the dosing chamber and the negative-pressure chamber. A fluid inlet may be in fluid communication with the dosing chamber, and a fluid outlet may be in fluid communication with the dosing chamber. A negative-pressure inlet may also be in fluid communication with the negative-pressure chamber. The cartridge can also include a biasing element coupled to the moveable barrier and operable to move the moveable barrier between a charge position and a discharge position. The negative-pressure source may be fluidly coupled to the negative-pressure inlet, and the fluid source may be fluidly coupled to the fluid inlet. Negative-pressure may be supplied to the negative-pressure chamber to move the moveable barrier to the charge position. In response to the supply of negative pressure, fluid may be drawn from the fluid source into the dosing chamber. The supply of negative pressure to the negative-pressure chamber may be stopped, and the biasing element may be actuated to move the moveable barrier to the discharge position to move fluid from the dosing chamber through the fluid outlet.

In yet further embodiments, an apparatus for providing instillation therapy with a negative-pressure source is described. The apparatus can include a housing having a dosing chamber and a negative-pressure chamber fluidly isolated from each other. The apparatus can also include a diaphragm disposed in the housing between the dosing chamber and the negative-pressure chamber and configured to move between a charge position and a discharge position in response to the application of negative-pressure to the negative-pressure chamber. A fluid inlet can be in fluid communication with the dosing chamber, and a fluid outlet can be in fluid communication with the dosing chamber. A negative-pressure inlet may be in fluid communication with the negative-pressure chamber. The apparatus can also include a fluid inlet valve fluidly coupled to the fluid inlet and a fluid outlet valve fluidly coupled to the fluid outlet.

In still other embodiments, a method for determining a mode of a therapy system is described. A negative pressure can be provided, and a rate of change of the negative pressure can be calculated. If the rate of change of the negative pressure exceeds a threshold rate of change of negative pressure, instillation therapy can be provided.

In still other embodiments, a method for determining a mode of a therapy system is described. A negative pressure can be provided, and a rate of change of the negative pressure can be calculated. If the rate of change of the negative pressure is less than a threshold rate of change of negative pressure, negative-pressure therapy can be provided.

In yet further embodiments, an apparatus for providing negative-pressure therapy and instillation therapy is described. The apparatus can include a negative-pressure source and a controller. The controller can be configured to calculate a rate of change of negative pressure generated by the negative-pressure source. The controller can also be configured to provide negative-pressure therapy if the rate of change of negative pressure is less than a threshold rate of change. The controller can be further configured to provide instillation therapy if the rate of change is greater than a threshold rate of change.

In yet another embodiment, an apparatus for providing instillation therapy with a negative-pressure source is described. The apparatus may include a housing having an ambient chamber and a negative-pressure chamber fluidly isolated from each other. The apparatus may also include a moveable barrier disposed in the housing between the ambient chamber and the negative-pressure chamber. A tube may be configured to be fluidly coupled to a fluid source and a dressing. The tube may pass through the ambient chamber. The apparatus may further include a negative-pressure inlet in fluid communication with the negative-pressure chamber; and a biasing element coupled to the moveable barrier. The biasing element may be operable to selectively permit fluid flow through the tube in response to operation of a negative-pressure source.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
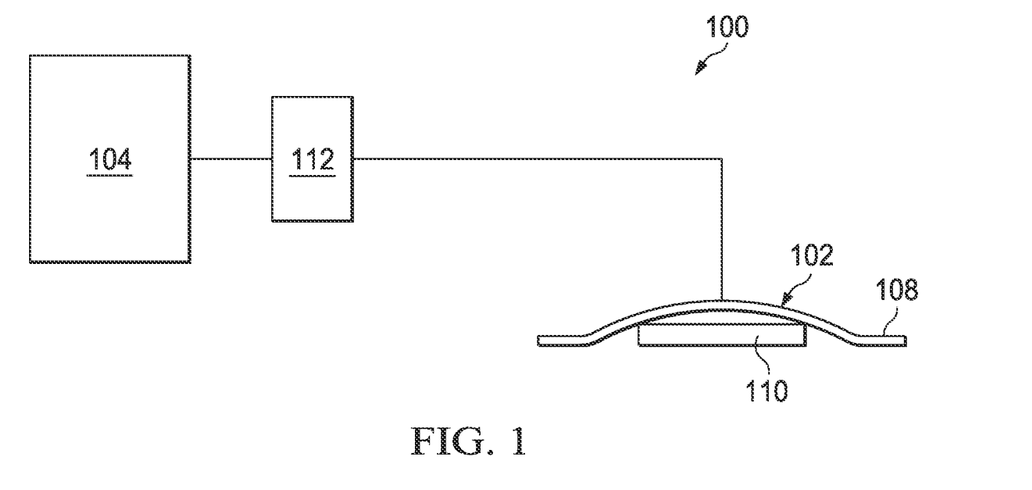
FIG. 1 is a functional block diagram of an example embodiment of a therapy system that can provide instillation fluid in accordance with this specification.

FIG. 1 is a simplified functional block diagram of an example embodiment of a therapy system 100 that can provide instillation therapy in accordance with this specification. The therapy system 100 may include a dressing and a negative-pressure source. For example, a dressing 102 may be fluidly coupled to a negative-pressure source 104, as illustrated in FIG. 1. A dressing generally includes a cover and a tissue interface. The dressing 102, for example, includes a cover 108, and a tissue interface 110. The therapy system 100 may also include a fluid management device, such as a cartridge 112, fluidly coupled to the dressing 102 and to the negative-pressure source 104.

In general, components of the therapy system 100 may be coupled directly or indirectly. For example, the negative-pressure source 104 may be directly coupled to the cartridge 112 and indirectly coupled to the dressing 102 through the cartridge 112. Components may be fluidly coupled to each other to provide a path for transferring fluids (i.e., liquid and/or gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. in some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a negative-pressure source, and conversely, the term "upstream" refers to a position relatively further away from a negative-pressure source. Similarly, it may be convenient to describe certain features in terms of fluid "inlet" or "outlet" in such a frame of reference. This orientation is generally presumed for purposes of describing various features and components of therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure source may include a user interface. A user interface may be a device configured to allow communication between a controller and an environment external to a negative-pressure source. In some embodiments, an external environment may include an operator or a computer system configured to interface with a negative-pressure source, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with a negative-pressure source. In some embodiments, a user interface may display information for an external environment such as a duration of therapy, a type of therapy, an amount of negative pressure being supplied, an amount of instillation solution being provided, a fluid level of a container, or a fluid level of a cartridge, for example.

A negative-pressure source may also include one or more pressure sensors. A pressure sensor, may be a piezoresistive strain gauge, a capacitive sensor, an electromagnetic sensor, a piezoelectric sensor, an optical sensor, or a potetrtiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure.

A negative-pressure source may include one or more controllers communicatively coupled to components of the negative-pressure source, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller: operating the valve; placing the valve in an open position, a closed position, or a metering position; and opening the valve, closing the valve, or metering the valve.

A controller may be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery back-up so that the non-volatile memory retains the programs or operational instructions if the PLC otherwise loses power. In some embodiments, a PLC may be configured to receive discrete signals and continuous signals and produce discrete and continuous signals in response.

A negative-pressure source may also include a power source. A power source may be a device that supplies electric power to an electric load. A power source may include a battery, a direct current (DC) power supply, an alternating current (AC) power supply, a linear regulated power supply, or a switched-mode power supply, for example. A power supply may supply electric power to a controller, a sensor, a flow meter, a valve, a user interface, or a pump, for example.

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Texas.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and caprolactone. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxyapatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square meter (gsm). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The dressing 102 may also be used to provide a sealed therapeutic environment for instillation therapy. Instillation therapy may include the slow introduction of a solution to a tissue site. The solution may be used to provide moisture to the tissue site, to provide warmth or cold to the tissue site, to provide a drug to the tissue site, or to provide another substance to the tissue site. Often, different types of instillation therapy may require a different type of instillation fluid to achieve a desired effect. For example, a first type of fluid may provide moisture to the tissue site. A different type of fluid may supply a drug to the tissue site. Many times, the need for different types of fluid to treat the tissue site may make instillation therapy time consuming to administer.

Some patients may experience improved outcomes with a combined treatment that includes using both negative-pressure therapy and instillation therapy. Existing therapy systems that provide instillation or irrigation of a tissue site as well as negative-pressure therapy can be complicated to use and setup. Multiple tubes, clamps, and interfaces may often be needed to properly apply both negative pressure and fluid to the tissue site. For example, to set up a therapy system having both negative-pressure therapy and instillation therapy, components for both systems may be placed proximate to a patient. Unfortunately, the cost of a combined treatment system can be prohibitive in many clinical environments, reducing the likelihood that a patient may receive the benefits of both systems.

In many clinical environments, negative-pressure therapy relies on a dedicated negative-pressure therapy system to provide negative-pressure therapy to a tissue site. The dedicated negative-pressure therapy system may be positioned proximate to a patient receiving negative-pressure therapy, and the dedicated negative-pressure therapy system may be fluidly coupled to a tissue site to provide negative-pressure therapy. Similarly, instillation therapy often relies on a dedicated instillation therapy system to provide instillation therapy to a tissue site. The dedicated instillation therapy system may also be positioned proximate to a patient receiving instillation therapy, and the dedicated instillation therapy device may be fluidly coupled to a tissue site to provide instillation therapy. Having both negative-pressure therapy system components and instillation therapy system components proximate to a patient may make the area around the patient cluttered, which can lead to negative outcomes for the patient.

Both dedicated negative-pressure therapy systems and dedicated instillation therapy systems may be expensive. Generally, given the costs associated with negative-pressure therapy and instillation therapy, medical facilities may not be willing to use capital to purchase both a dedicated negative-pressure therapy system and a dedicated instillation therapy system. As a result, some clinical facilities may choose to forgo some types of clinical treatment. For example, some clinical facilities may maintain a dedicated negative-pressure therapy system to provide negative-pressure therapy. If a patient requires instillation therapy, a clinician may be required to physically administer instillation therapy, such as with a syringe. Application of instillation therapy in this manner may also require the clinician to remove the dressing, which can cause pain to the patient and potentially increase infection risks. Physical administration of instillation therapy can require a significant investment of clinician time, increase the likelihood of misapplication of therapy, and potentially increase the risk of infection of a tissue site.

Some clinical facilities employ multi-channel dedicated negative-pressure therapy systems. A multi-channel negative-pressure therapy system may be capable of providing negative-pressure therapy to more than one tissue site at a time. A multi-channel negative-pressure therapy system may be large and inhibit placement of other devices near a patient. If instillation therapy is also needed, it may be difficult to place a dedicated instillation therapy system proximate to a patient. Consequently, a clinician may be required to physically administer instillation therapy, which can cause some or all of the complications previously described.

The therapy system 100 described herein can solve these problems and others by managing negative-pressure to deliver instillation fluids. In some embodiments, the therapy system 100 can provide negative-pressure therapy to the tissue site. For example, the therapy system 100 can be fluidly coupled to the dressing 102 to provide negative-pressure therapy to a tissue site. In some embodiments, the therapy system 100 can provide instillation therapy to the tissue site. For example, the cartridge 112 can be fluidly coupled to the dressing 102 and the negative-pressure source 104 to use the therapy system 100 to provide instillation therapy.

Figure 2:
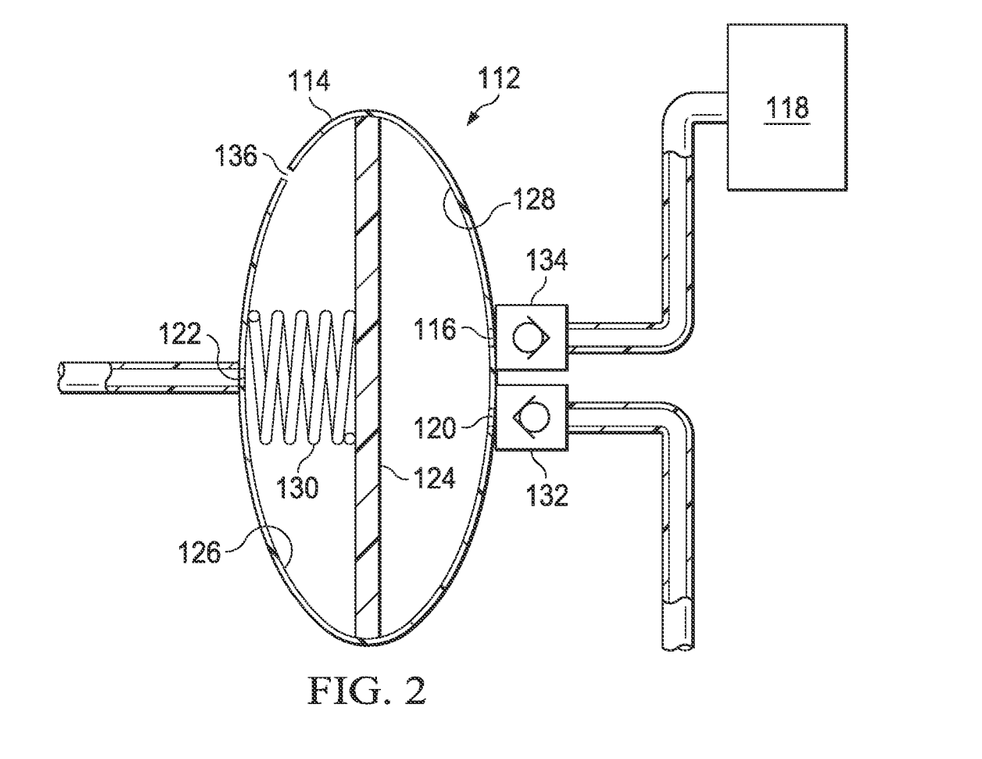
FIG. 2 is a schematic sectional diagram illustrating additional details that may be associated with an example embodiment of a cartridge of the therapy system of FIG. 1.

FIG. 2 is a schematic sectional diagram, illustrating additional details that may be associated with some example embodiments of the cartridge 112. Generally, the cartridge 112 may have many different shapes and sizes. In some embodiments, the cartridge 112 may be manufactured to physically couple to existing negative-pressure therapy products. For example, the cartridge 112 and the components described below, may be manufactured to resemble a canister, such as a Bemis canister that can be coupled to the negative-pressure source 104. In other embodiments, the cartridge 112 may be manufactured to resemble a canister for a V.A.C. ULTA™ negative-pressure wound therapy system manufactured by Kinetic Concepts, Inc. The embodiments described and illustrated below are schematic representations, and the shape of the cartridge 112 may vary.

The cartridge 112 may have a housing 114. In some embodiments, the housing 114 may form an outer portion of the cartridge 112. In other embodiments, the housing 114 may be disposed inside another container so that the housing 114 may be enclosed in the cartridge 112. In some embodiments, the housing 114 may generally define a chamber and have a structural arrangement to fluidly isolate the chamber from the ambient environment. In some embodiments, the housing 114 may be ovoid in shape and form an ovoid chamber having an oval cross-section. In other embodiments, the housing 114 may have other suitable shapes, such as spherical, cuboid, or amorphous shapes that form similarly shaped chambers having similarly shaped cross-sections. In some embodiments, the shape of the chamber may not correspond with the shape of the housing 114. In some embodiments, the housing 114 may be formed of EASTAR™ DN004 produced by Eastman Chemical Company. In other embodiments, the housing 114 may be formed of Terlux® 2802HD or Terlux® 2822HD produced by Styrolution Group GmbH.

In some embodiments, a barrier may be disposed within the chamber of the housing 114. A barrier may be a solid object positioned within the chamber of the housing 114 to divide the chamber of the housing 114 into two separate fluid chambers. In some embodiments, a portion or an entirety of a barrier may be movable, such as a piston or a diaphragm 124, to adjust respective volumes of the chambers created by the barrier. In some embodiments, the diaphragm 124 may be a membrane or a sheet of semi-flexible material having a periphery. The periphery of the diaphragm 124 may be coupled to the housing 114 to form a negative-pressure chamber 126 and a dosing chamber 128. Generally, the periphery of the diaphragm 124 may be coupled to the housing 114 so that the negative-pressure chamber 126 is fluidly isolated from the dosing chamber 128. For example, the diaphragm 124 may be sealed to the housing 114, may be welded to the housing 114, or may be otherwise coupled to the housing 114 to prevent fluid movement across the diaphragm 124. In some embodiments, the diaphragm 124 may be formed of an elastic or a semi-elastic material. In some embodiments, the diaphragm 124 may be formed of rubber, thermoplastic, or polytetrafluoroethylene.

In some embodiments, the periphery of the diaphragm 124 may be coupled to the housing 114 so that the diaphragm 124 may flex between a discharge position and a charge position. The discharge position of the diaphragm 124 may be the position of the diaphragm 124 that maximizes the volume of the negative-pressure chamber 126 and minimizes the volume of the dosing chamber 128. The charge position of the diaphragm 124 may be the position of the diaphragm 124 that maximizes the volume of the dosing chamber 128 and minimizes the volume of the negative-pressure chamber 126. In some embodiments, the periphery of the diaphragm 124 may be coupled proximate to a center of a cross-section of the housing 114. For example, the housing 114 may form an ovoid or elliptical-shaped chamber having a transverse diameter and a conjugate diameter. In some embodiments, the periphery of the diaphragm 124 may be coupled to the housing 114 so that the diaphragm 124 coincides with the transverse diameter if the volumes of the negative-pressure chamber 126 and the dosing chamber 128 are equal, as shown in FIG. 2. In other embodiments, the diaphragm 124 may be coupled to the housing 114 in other locations of the housing 114.

In some embodiments, the dimensions of the diaphragm 124, the negative-pressure chamber 126, and the dosing chamber 128 may be determined by the amount of fluid needed to provide instillation. For example, a tissue site may need approximately 5 milliliters of fluid to be dispensed with each operation of the cartridge 112. Consequently, the dosing chamber 128 may have a volume of about 5 milliliters if the diaphragm 124 is in the charged position, and the negative-pressure chamber 126 may have a volume of about 5 milliliters if the diaphragm 124 is in the discharge position. If the housing 114 is spherical, then the dosing chamber 128 may have a radius given by:

$$\frac{4}{3}\pi \times r^3 \equiv V$$

where r is the radius of a sphere in millimeters and V is the volume of the sphere in milliliters. For an exemplary 5 milliliter volume, the radius of the dosing chamber 128 if the diaphragm 124 is in the charge position is about 10.6 millimeters. In some embodiments, the diaphragm 124 may have a radius approximately equal to the radius of the dosing chamber 128 if the diaphragm 124 is in the charge position. Similarly, the negative-pressure chamber 126 may have a radius of about 10.6 millimeters if the diaphragm 124 is in the discharge position. In some embodiments, the volume of the dosing chamber 128 if the diaphragm 124 is in the charge position is between about 5 milliliters and about 10 milliliters. In other embodiments, the volume of the dosing chamber 128 may be varied as need to administer a therapeutic amount of fluid to a tissue site.

In some embodiments, the housing 114 may be formed of two sheets of a polymer film having peripheral portions. The peripheral portions of each sheet may be coupled together, such as by welding, adhering, or otherwise securing the peripheral portions of each sheet to each other. In some embodiments, a third sheet of polymer material may be disposed between the first sheet and the second sheet of polymer material. The third sheet may have peripheral portions coupled to the peripheral portions of the first and second sheet of polymer material to form the diaphragm 124, the negative-pressure chamber 126, and the dosing chamber 128.

In some embodiments, the housing 114 may have a negative-pressure inlet 122. The negative-pressure inlet 122 may be a fluid passage formed in the housing 114 to provide fluid communication with the negative-pressure chamber 126. In some embodiments, the negative-pressure inlet 122 may be a tube having at least one lumen. The tube may be coupled to the housing 114 so that the lumen of the tube is in fluid communication with the negative-pressure chamber 126. In some embodiments, the negative-pressure inlet 122 may be further fluidly coupled to the negative-pressure source 104.

In some embodiments, the housing 114 may have a vent 136. The vent 136 may be an opening formed in the housing 114. In some embodiments, the vent 136 may be in fluid communication with the negative-pressure chamber 126. In some embodiments, the vent 136 may fluidly couple the negative-pressure chamber 126 to the ambient environment. In some embodiments, the vent 136 may be sized so that fluid may flow out of the negative-pressure chamber 126 through the negative-pressure inlet 122 faster than fluid in the ambient environment may flow into the negative-pressure chamber 126 through the vent 136.

In some embodiments, the diaphragm 124 may be biased to the discharge position. For example, a biasing element may be disposed in the negative-pressure chamber 126 to bias the diaphragm 124 to the discharge position. A biasing element may be a spring 130, for example. The spring 130 may have a first end coupled to the housing 114 and a second end coupled to the diaphragm 124. The spring 130 may have an unloaded position and a loaded position. Generally, if no external force is acting on the spring 130, the spring 130 is in the unloaded position. If the spring 130 is compressed or extended, the spring 130 may be in the loaded position. Generally, a spring may exert a reactive force in response to displacement from the unloaded position. The reactive force is generally proportional to the distance a spring is either compressed or extended if an external force loads the spring. As shown in FIG. 2, the spring 130 may be partially compressed or partially loaded.

In some embodiments, the biasing element may be a foam disposed in the negative-pressure chamber 126. In some embodiments, the foam may be an open-cell reticulated foam having a spring rate similar to the spring 130. In some embodiments, for example, if the housing 114 comprises a cylindrical construction, the foam may be configured to compress along a length of the cylinder in response to the application of negative pressure.

In some embodiments, the cartridge 112 may include a fluid inlet 116. The fluid inlet 116 may be a fluid passage coupled to the housing 114. In some embodiments, the fluid inlet 116 may be a tube having at least one lumen. The tube may be coupled to the housing 114 so that the at least one lumen of the tube is in fluid communication with the dosing chamber 128. In some embodiments, the fluid inlet 116 may be further fluidly coupled to a fluid source 118. The fluid source 118 may be a reservoir of fluid, such as instillation fluid, for example. In some embodiments, the fluid source 118 may be a reservoir of fluid suspended from an intravenous pole proximate to the negative-pressure source 104 or the cartridge 112. In some embodiments, the fluid source 118 may an intravenous bag having instillation fluid stored therein.

In some embodiments, a valve 134 may be fluidly coupled to the fluid inlet 116. In some embodiments, the valve 134 may be coupled to the housing 114, and the fluid inlet 116 may be coupled to the valve 134 so that the valve 134 is fluidly coupled between the fluid inlet 116 and the fluid source 118. In other embodiments, the valve 134 may be coupled in other locations. In some embodiments, the valve 134 is a check valve. A check valve may be a valve that permits one-way flow of fluid through the valve. In some embodiments, the valve 134 may be fluidly coupled to the fluid inlet 116 to permit fluid flow through the fluid inlet 116 into the dosing chamber 128 and prevent fluid flow from the dosing chamber 128.

In some embodiments, the cartridge 112 may also have a fluid outlet 120. The fluid outlet 120 may be a fluid passage coupled to the housing 114 to provide fluid communication with the dosing chamber 128. In some embodiments, the fluid outlet 120 may be a tube having at least one lumen. The tube may be coupled to the housing 114 so a lumen is in fluid communication with the dosing chamber 128. In some embodiments, the fluid outlet 120 may be further fluidly coupled to a dressing, such as the dressing 102. If the fluid outlet 120 is fluidly coupled to the dressing 102, the dressing 102 may be in fluid communication with the dosing chamber 128 through the fluid outlet 120.

In some embodiments, a valve 132 may be fluidly coupled to the fluid outlet 120 to control fluid flow through the fluid outlet 120. In some embodiments, the valve 132 may be coupled to the housing 114, and the fluid outlet 120 may be coupled to the valve 132 so that the valve 132 is fluidly coupled between the fluid outlet 120 and the dosing chamber 128. In other embodiments, the valve 132 may be coupled in other locations. In some embodiments, the valve 132 is a check valve. In some embodiments, the valve 132 may be fluidly coupled to the fluid outlet 120 to prevent fluid flow through the fluid outlet 120 into the dosing chamber 128 and permit fluid flow from the dosing chamber 128 into the fluid outlet 120.

Figure 3:
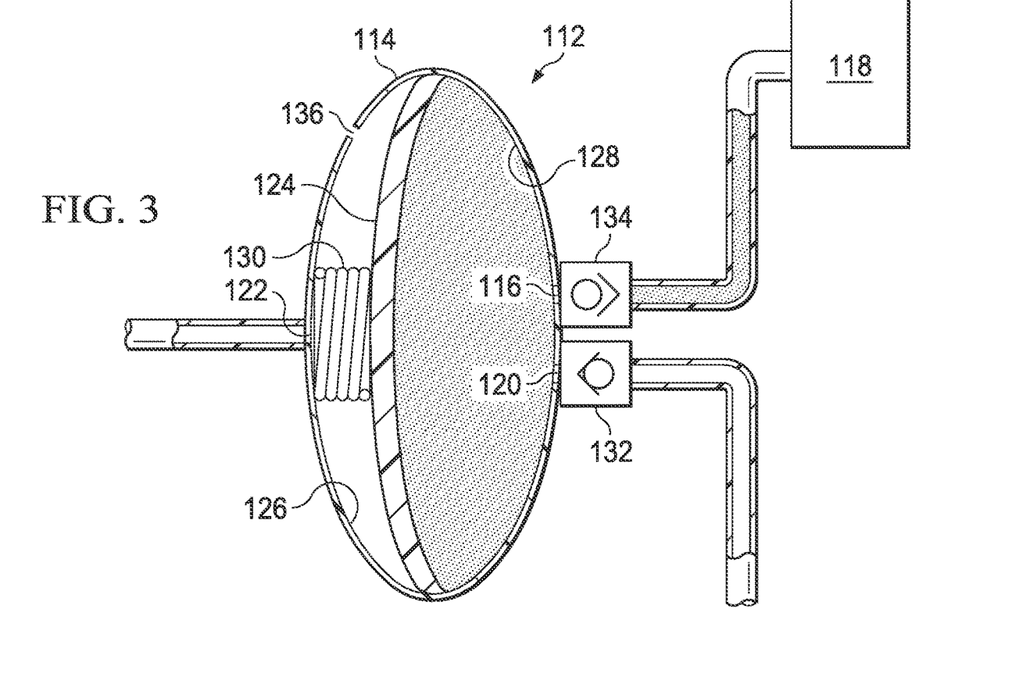
FIG. 3 is a schematic sectional diagram illustrating additional details that may be associated with an operative embodiment of the cartridge of FIG. 2.

FIG. 3 is a schematic sectional diagram illustrating additional details that may be associated with some example embodiments of the cartridge 112. As shown in FIG. 3, the spring 130 may be in the loaded position, and the diaphragm 124 may be in the charge position. In operation, the negative-pressure source 104 may generate a negative-pressure in the negative-pressure chamber 126 by drawing fluid from the negative-pressure chamber 126 through the negative-pressure inlet 122. Consequently, a negative-pressure may be generated in the negative-pressure chamber 126. As a negative pressure is generated in the negative-pressure chamber 126, the increasing pressure differential between the negative-pressure chamber 126 and the dosing chamber 128 may cause the diaphragm 124 to move toward the negative-pressure inlet 122. Generally, the spring constant of the spring 130 may be selected so that a predetermined negative pressure generated by the negative-pressure source 104 exerts a greater force on the diaphragm 124 than the reactive force of the spring 130. The predetermined negative pressure may be associated with a fluid flow rate of the negative-pressure source. In response, the movement of the diaphragm 124 toward the negative-pressure inlet 122 compresses the spring 130 from the unloaded position to the loaded position.

Fluid at ambient pressure surrounding the housing 114 may flow into the negative-pressure chamber 126 through the vent 136 if a negative pressure is generated in the negative-pressure chamber 126. In some embodiments, the negative-pressure source 104 may draw fluid from the negative-pressure chamber 126 faster than the fluid at ambient pressure may flow into the negative-pressure chamber 126 through the vent 136.

In response to the movement of the diaphragm 124 toward the negative-pressure inlet 122, the volume of the dosing chamber 128 may increase. An increase in the volume of the dosing chamber 128 may generate a negative pressure in the dosing chamber 128 that can draw fluid into the dosing chamber 128 through the fluid inlet 116 and the fluid outlet 120. The valve 132 may be closed to prevent the flow of fluid into the dosing chamber 128 through the fluid outlet 120, and the valve 134 may be opened to allow the flow of fluid into the dosing chamber 128 through the fluid inlet 116. In response, fluid may flow from the fluid source 118, through the fluid inlet 116, and into the dosing chamber 128. In some embodiments, the dosing chamber 128 may be sized to hold a predetermined dose of instillation fluid for instillation of a tissue site.

example, if the diaphragm 124 is in the charge position illustrated in FIG. 3, the dosing chamber 128 may have a volume substantially equal to the amount of fluid necessary to provide a therapeutic dose of instillation fluid to a tissue site. A therapeutic dose of instillation fluid may be a volume of fluid prescribed to be delivered to a tissue site to provide suitable therapeutic benefits to the tissue site. In other embodiments, the volume of the dosing chamber 128 may be larger or smaller than the therapeutic dose of instillation fluid.

Figure 4:
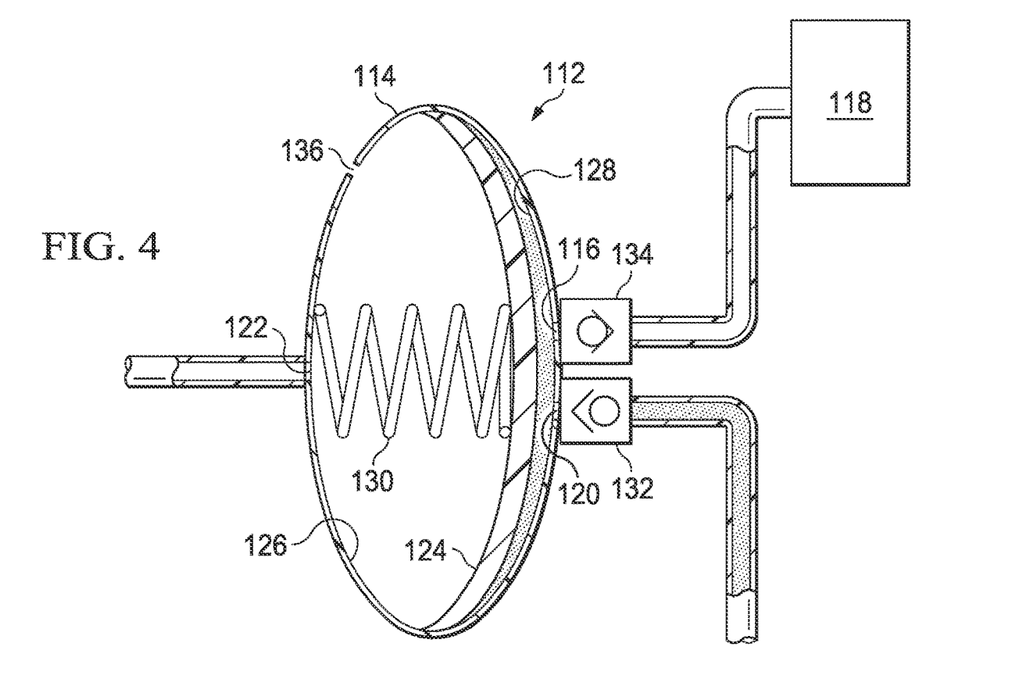
FIG. 4 is a schematic sectional diagram illustrating additional details that may be associated with an operative embodiment of the cartridge of FIG. 2.

FIG. 4 is a schematic sectional diagram illustrating additional details that may be associated with some example embodiments of the cartridge 112. As shown in FIG. 4, the spring 130 is in the unloaded position, and the diaphragm 124 is in the discharge position. If the diaphragm 124 is in the charge position of FIG. 3 and the dosing chamber 128 is substantially filled with instillation fluid, the negative-pressure source 104 may be stopped so that the negative-pressure source 104 is no longer drawing fluid from the negative-pressure chamber 126. In response, fluid under ambient pressure surrounding the housing 114 may flow through the vent 136 into the negative-pressure chamber 126. The flow of fluid through the vent 136 decreases the negative pressure in the negative-pressure chamber 126. As the negative pressure decreases, the reactive force generated by the compression of the spring 130 may overcome the force exerted by the pressure differential between the negative-pressure chamber 126 and the dosing chamber 128, causing the diaphragm 124 to move toward the fluid outlet 120 and the discharge position. As the reactive force of the spring 130 moves the diaphragm 124 toward the fluid outlet 120, the diaphragm 124 may compress the fluid in the dosing chamber 128. If the valve 134 is closed and the valve 132 is open, fluid may flow from the dosing chamber 128, through the fluid outlet 120, and to the dressing 102 to provide instillation therapy.

In some embodiments, the spring 130 may be disposed in the dosing chamber 128. If the spring 130 is disposed in the dosing chamber 128, the spring 130 may be in an unloaded position if the diaphragm 124 is in the discharge position, and the spring 130 may be in a loaded position if the diaphragm 124 is in the charge position. Operation of the negative-pressure source 104 may cause the diaphragm 124 to extend the spring 130, and the cessation of operation of the negative-pressure source 104 may allow the spring 130 to draw the diaphragm 124 to the discharge position.

Figure 5:
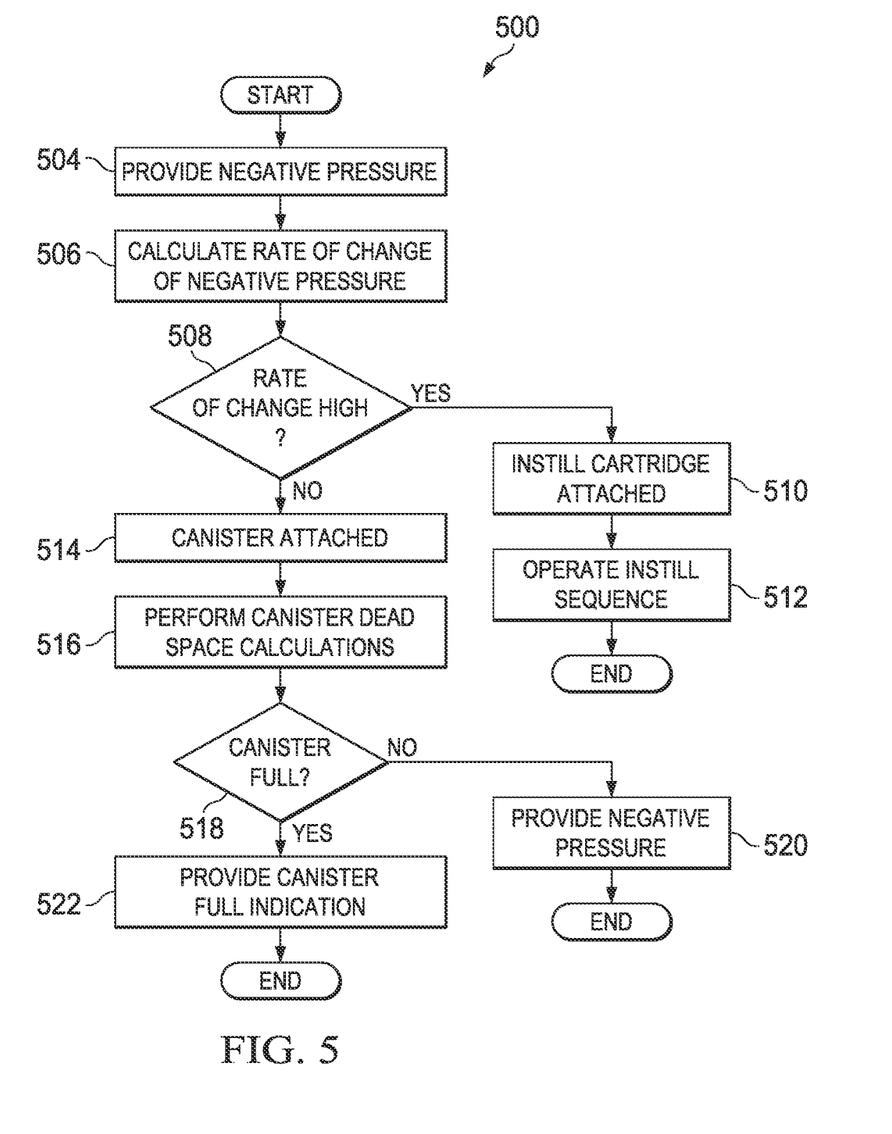
FIG. 5 is a flow chart depicting logical operational steps of a method for providing instillation therapy in accordance with some embodiments.

FIG. 5 is a flow chart 500 illustrating exemplary logical operations that can be implemented in some embodiments of the therapy system 100 of FIG. 1. For example, the operations may be implemented by a controller operably associated with a negative-pressure source, such as the negative-pressure source 104, configured to execute the operations. In some embodiments, the negative-pressure source 104 may have a mechanical apparatus adapted to be operated by a clinician for the selection of instillation or negative-pressure therapy. In some embodiments, the negative-pressure source 104 may include software or other control devices to determine if a canister for the collection of fluid from the tissue site is fluidly coupled to the negative-pressure source 104. The negative-pressure source 104 may also include software or other control devices to determine if a fluid instillation cartridge is fluidly coupled to the negative-pressure source 104. In these embodiments, the negative-pressure source 104 may then provide negative-pressure therapy or instillation therapy based on the determination of the type of apparatus fluidly coupled to the negative-pressure source 104.

At block 504, a negative-pressure source may be operated to provide negative pressure to the cartridge. For example, a controller of the negative-pressure source 104 may operate the negative-pressure source 104. At block 506, a rate of change of negative-pressure may be calculated. For example, a controller of the negative-pressure source 104 may calculate the rate of change of negative pressure based on one more pressure readings from a pressure sensor located in the negative-pressure source 104. In some embodiments, the rate of change of negative pressure may indicate how quickly or slowly the negative pressure in the negative-pressure chamber 126 is increasing within a time period. In some embodiments, the time period may be predetermined. For example, the time period may correspond to a known amount of time that may be required to evacuate a canister. At block 508, it can be determined if the rate of change of the negative pressure is greater than a threshold rate of change of the negative pressure. In some embodiments, if a canister for negative-pressure therapy is fluidly coupled to the negative-pressure source 104, the rate of change of negative pressure may be within a predetermined range. Similarly, if the cartridge 112 is fluidly coupled to the negative-pressure source 104, the rate of change of negative pressure may fall within a different predetermined range. For example, a canister for negative-pressure therapy may have a larger volume than the negative-pressure chamber 126 of the cartridge 112. Because the canister has a larger volume, the predetermined rate of change of negative pressure may be lower than the predetermined rate of change of negative pressure for the cartridge 112. For example, a controller of the negative-pressure source 104 may determine if the rate of change of negative pressure is within the predetermined rate of change for the cartridge 112, that is, high. In other embodiments, a controller of the negative-pressure source 104 may be programmed to compare the rate of change of negative pressure to a threshold rate of change of negative pressure for the cartridge 112. If a controller is programmed to compare the rate of change of negative-pressure to the threshold rate of change of negative pressure for the cartridge 112, a controller may determine if the rate of change of negative pressure is less the threshold rate of change of negative pressure, that is, low.

If rate of change of the negative pressure exceeds the threshold, it may be inferred at block 510 that a cartridge for providing instillation therapy is fluidly coupled to the negative-pressure source. For example, a controller of the negative-pressure source 104 may determine that the cartridge 112 is fluidly coupled to the negative-pressure source 104. At block 512, a negative-pressure source may be operated in an instill mode or an instill sequence to provide instillation therapy to a tissue site. For example, a controller of the negative-pressure source 104 may operate the negative-pressure source 104 and the cartridge 112 as described above with respect to FIGS. 2-4 to provide instillation therapy to a tissue site.

At block 508, if the rate of change of negative pressure is less than the threshold, it may be inferred at block 514 that a canister for negative-pressure therapy is fluidly coupled to the negative-pressure source. For example, a controller of the negative-pressure source 104 may determine that a canister for negative-pressure therapy is fluidly coupled to the negative-pressure source 104. At block 516, the empty volume of the canister or "dead space" can be calculated. For example, a controller of the negative-pressure source 104 may perform dead space calculations for the canister. In some embodiments, the amount of dead space in a canister may be calculated by supplying a negative-pressure to the canister and then venting the canister for about 1 second. The corresponding rise in pressure during the 1 second interval is monitored to determine the empty volume of the canister. At block 518, the calculations of the dead space can be used to determine if a fluidly coupled canister is full. For example, a controller of the negative-pressure source 104 can determine if a fluidly coupled canister is full.

At block 518, if the canister is not full, a negative-pressure source can provide negative-pressure therapy at block 520. For example, a controller of the negative-pressure source 104 can operate the negative-pressure source 104 to provide negative-pressure therapy to a tissue site. At block 518, if the canister is full, a full canister indication may be provided at block 522. For example, a controller may provide a full canister indication on a user interface of the negative-pressure source 104.

Figure 6:
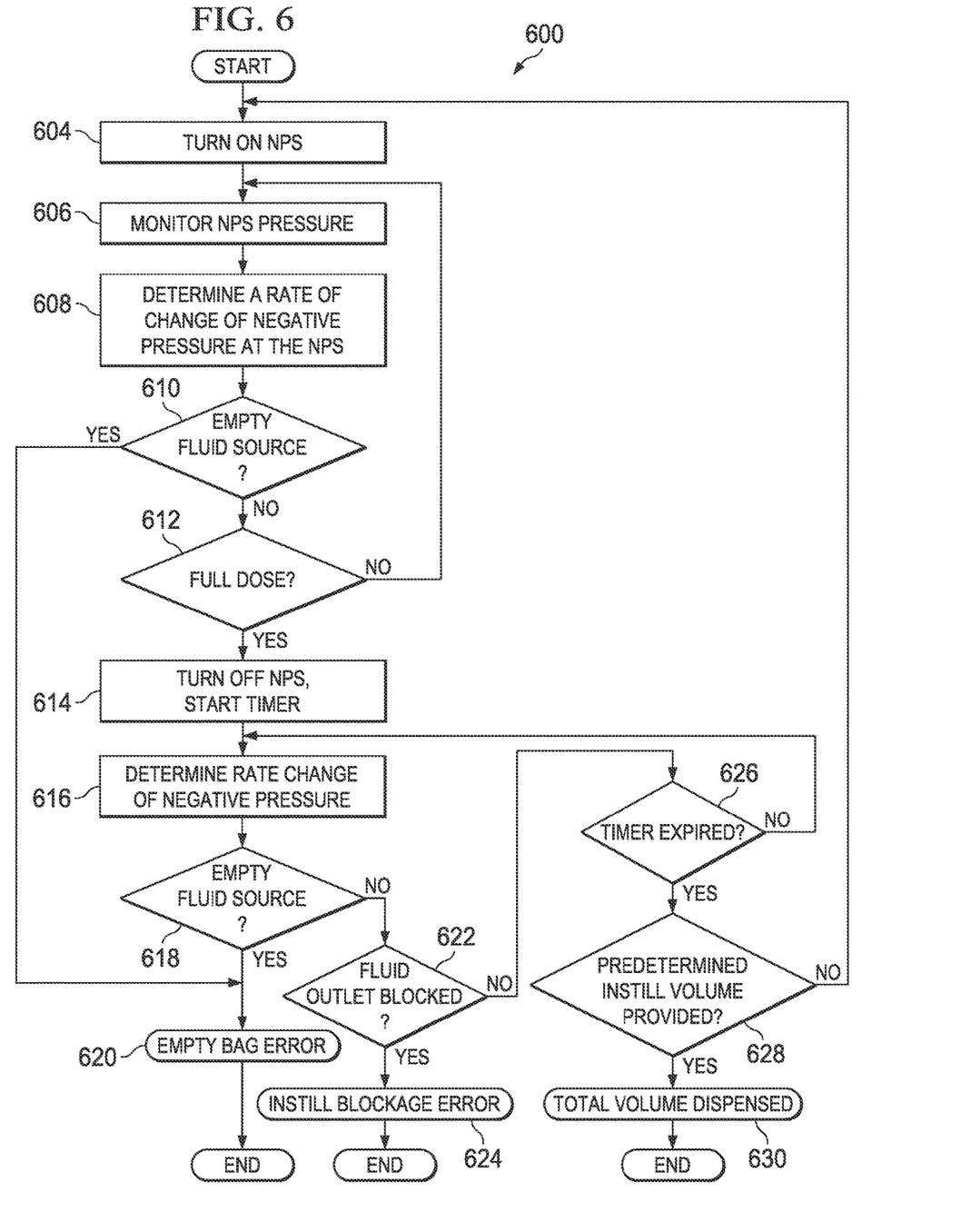
FIG. 6 is a flow chart depicting logical operational steps of another method for providing instillation therapy in accordance with some embodiments.

FIG. 6 is a flow chart 600 illustrating exemplary logical operations that can be implemented in some embodiments of the therapy system 100 of FIG. 1. For example, the operations may be implemented by a controller in a negative-pressure source, such as the negative-pressure source 104, configured to execute the operations. At block 604, a negative-pressure source may be turned on. For example, a controller of the negative-pressure source 104 may turn on a pump in the negative-pressure source 104 to generate a negative pressure in the cartridge 112.

At block 606 the pressure at the negative-pressure source may be monitored. For example, a controller of the negative-pressure source 104 may monitor the pressure at the pump in the negative-pressure source 104 for a time interval, which may be predetermined. For example, the time interval may correspond to a known amount of time that may be required to fill the dosing chamber 128 of the cartridge 112 with a dose of instillation fluid. At block 608, the rate of change of the negative pressure at the negative-pressure source can be determined. For example, a controller of the negative-pressure source 104 may monitor the rate of change of negative pressure at the negative-pressure source 104 for the time interval. A controller of the negative-pressure source 104 may determine the rate of change of the negative pressure during the predetermined time. At block 610, the rate of change of the pressure during the predetermined time may indicate if a fluid source, such as the fluid source 118 is empty. For example, if the rate of change of the negative pressure is greater than a threshold rate of change of the negative pressure during the time interval, it can be inferred that the fluid source 118 may be empty.

At block 610, if the fluid source is empty, an empty bag error may be provided at block 620. For example, a controller may provide an empty bag error on a user interface of the negative-pressure source 104. At block 610, if the fluid source is not empty, it can be determined at block 612 if a dose of fluid has filled the cartridge. Generally, if the pressure in the negative-pressure source 104 is stable, that is, maintaining a predetermined pressure within predetermined tolerances, the diaphragm 124 in the cartridge 112 may be positioned in the charge position adjacent to the negative-pressure inlet 122. The predetermined pressure and predetermined tolerances may be based on known pressures that can be provided by the negative-pressure source 104. In some embodiments, the predetermined pressure may be about −100 mm Hg having a tolerance of about +/−10 mm Hg. For example, a controller of the negative-pressure source 104 may determine that the pressure is stable to determine if dose of fluid has filled the dosing chamber 128 of the cartridge 112. If a dose of fluid has not filled the cartridge, a pressure at the negative-pressure source can be monitored at block 606.

At block 612, if a dose of fluid has filled the cartridge, the negative-pressure source 104 may be turned off and a timer may be started. For example, a controller of the negative-pressure source 104 can turn off the negative-pressure source 104 and start a timer in the negative-pressure source 104. In response, a biasing element, such as the spring 130 may exert a reactive force on the diaphragm 124, causing fluid to flow from the cartridge 112 to the tissue site as described above with respect to FIG. 4. At block 616, the rate of change of negative pressure in the negative-pressure source can be determined. For example, a controller of the negative-pressure source 104 can monitor the rate of change of negative pressure at the negative-pressure inlet 122 via a pressure sensor fluidly coupled to the negative-pressure inlet 122. If fluid is flowing from the dosing chamber 128 through the fluid outlet 120, the negative pressure in the negative-pressure chamber 126 may change at an expected rate. The expected rate may be based on the spring constant of the spring 130, the size of the vent 136, and the size of the dosing chamber 128. If the rate of change of pressure is greater than or less than the expected rate of change of negative pressure associated with normal dosage of instillation fluid by the spring 130 and the diaphragm 124, an error may have occurred. For example, if the rate of change of negative pressure is greater than the expected rate of change of negative pressure, the fluid source 118 may be empty. If the rate of change of pressure is less than the expected rate of change of pressure or does not change, the fluid outlet 120 may be blocked.

At block 618, if the fluid source is empty, and an empty bag error may be provided at block 620. For example, a controller of the negative-pressures source may provide an empty bag error with a user interface of the negative-pressure source 104. At block 618, if the fluid source is not empty, a negative-pressure source may determine if the fluid outlet is blocked at block 622. For example, a controller of the negative-pressure source 104 may determine if the fluid outlet 120 is blocked. If the fluid outlet is blocked an instill blockage error may be provided at block 624. For example, a controller may provide an instill blockage error on the user interface of the negative-pressure source 104.

100861 At block 622, if the fluid outlet is not blocked, the negative-pressure source determines if the timer has expired at block 626. If the timer has not expired, the rate of change of negative pressure may be determined at block 616. For example, a controller of the negative-pressure source 104 can determine if the timer, started when the pump was stopped, has reached a predetermined time. The predetermined time may be based on an expected time interval for the fluid in the dosage chamber 128 to flow through the fluid outlet 120. At block 626, if the timer has expired, the negative-pressure source can determine if the total volume has been provided. For example, a controller of the negative-pressure source 104 can include a counter that increments upwards each time the pump of the negative-pressure source 104 is operated during the instillation therapy cycle. If the volume of the dosing chamber 128 when the diaphragm 124 is in the charge position is known, a controller can determine the total volume of fluid provided through the fluid outlet 120. A controller can then compare the total volume of fluid provided to a predetermined volume of instillation fluid to be provided to determine if the predetermined volume of instillation fluid required has been provided. The predetermined volume of instillation fluid required may be based on a total volume prescribed by a clinician. At block 628, if the predetermined volume of instillation fluid has not been provided, the negative-pressure source may be turned on at block 604. At block 628, if the predetermined volume of instillation fluid has been provided, a total volume dispensed indication can be provided. For example, a controller may provide a total volume dispensed indication on the user interface of the negative-pressure source 104.

Figure 7:
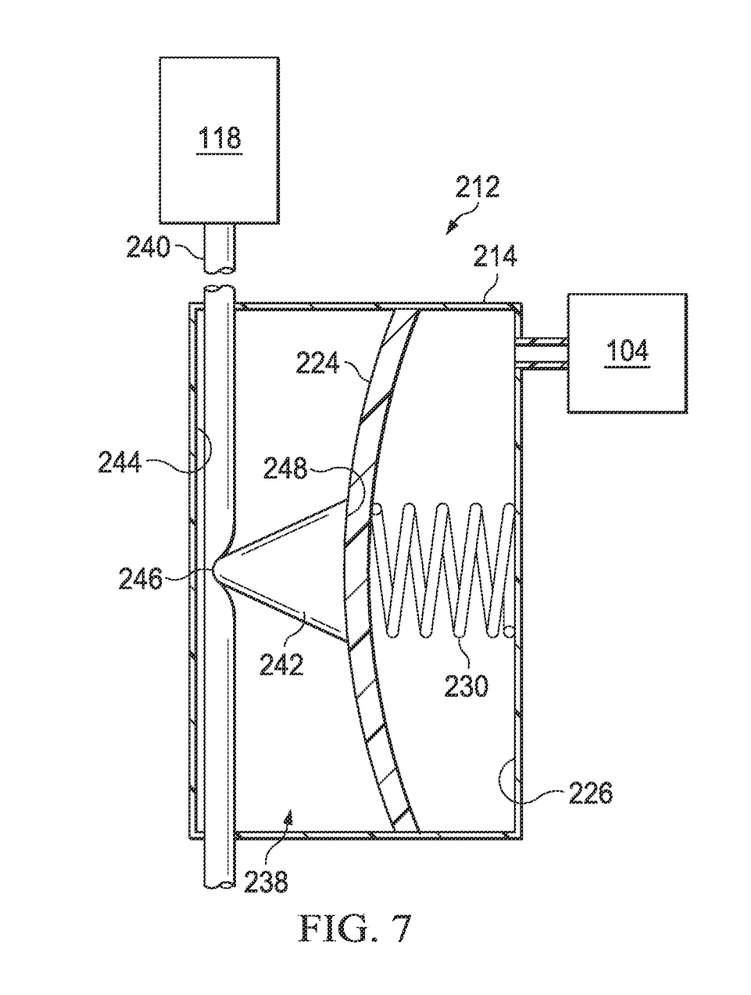
FIG. 7 is a schematic sectional diagram illustrating details that may be associated with another embodiment of a cartridge.

FIG. 7 is a schematic diagram of another cartridge 212, illustrating details that may be associated with some example embodiments. The cartridge 212 may be similar to and include elements of the cartridge 112. Similar elements may have similar reference numbers that are indexed to 200. In some embodiments, the cartridge 212 may include a housing 214 having a negative-pressure chamber 226 and an ambient chamber 238 formed by a diaphragm 224. A biasing member, such as a spring 230, may be disposed in the negative-pressure chamber 226 and may be operatively coupled to the diaphragm 224. In some embodiments, the diaphragm 224 may have a pinch valve, such as a boss 242 coupled to the diaphragm 224. In some embodiments, the boss 242 may be coupled to the diaphragm 224 so that the boss 242 is disposed in the ambient chamber 238. In some embodiments, a tube 240 may pass through the ambient chamber 238 and may be fluidly coupled to the fluid source 118 and the dressing 102. In some embodiment, the fluid source 118 may be fluidly coupled so that gravity may urge fluid to flow from the fluid source 118 to the cartridge 212. In some embodiments, the negative-pressure source 104 may be fluidly coupled to the negative-pressure chamber 226.

In some embodiments, the housing 214 may be similar to and operate as described with respect to the housing 114. Similarly, the diaphragm 224, the spring 230, and the negative-pressure chamber 226 may be similar to and operate as described with respect to the diaphragm 124, the spring 130, and the negative-pressure chamber 126.

In some embodiments, the ambient chamber 238 may be configured to receive the tube 240. The ambient chamber 238 may be open to the ambient environment so that a pressure in the ambient chamber 238 may be substantially the same as a pressure in the ambient environment. In some embodiments, the ambient chamber 238 may have a wall 244. The wall 244 may be positioned opposite of the diaphragm 224. In some embodiments, the tube 240 may pass through the ambient chamber 238, and the wall 244 may be substantially parallel to an axis of the tube 240.

In some embodiments, the boss 242 may be a solid body having a triangularly shaped cross section, an apex 246, and a base 248. The base 248 may be coupled to the diaphragm 224 so that the apex 246 is proximate to the wall 244 of the ambient chamber 238. In some embodiments, the apex 246 of the boss 242 may be rounded. In some embodiments, the boss 242 may be coupled to the diaphragm 224 so that the boss 242 may move with the diaphragm 224.

In some embodiments, the spring 230 may be biased so that if the tube 240 passes through the ambient chamber 238, the boss 242 may engage the tube 240. If the boss 242 engages the tube 240, the boss 242 may compress the tube 240 against the wall 244. Compression of the tube 240 may restrict fluid flow through the tube 240.

Figure 8:
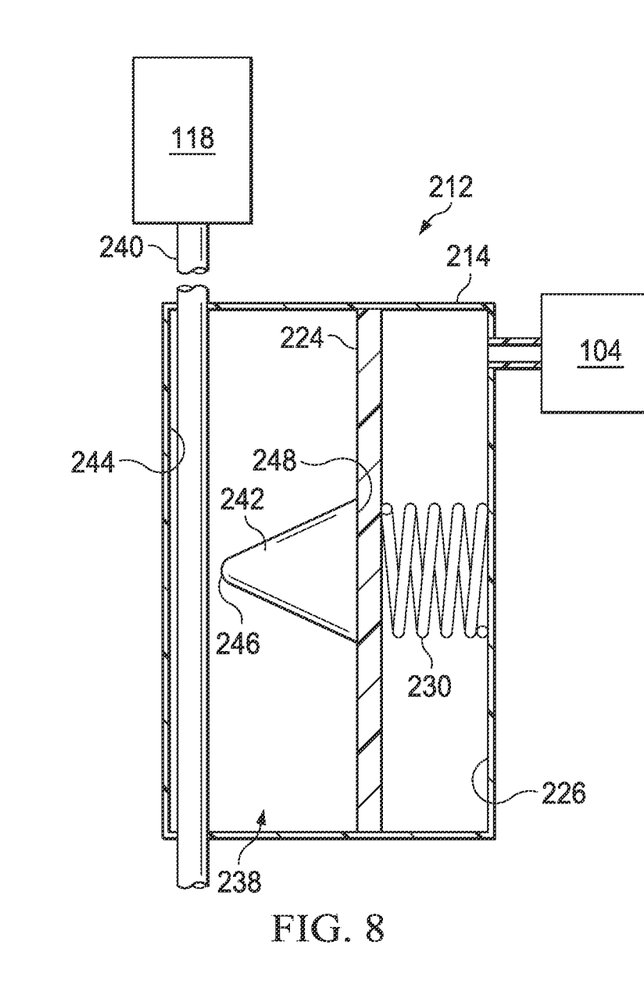
FIG. 8 is a schematic sectional diagram illustrating additional details that may be associated with an operative embodiment of the cartridge of FIG. 7.

FIG. 8 is a schematic diagram illustrating additional details that may be associated with some example embodiments of the cartridge 212. In some embodiments, the negative-pressure source 104 may be operated to draw fluid from the negative-pressure chamber 226. As fluid is drawn from the negative-pressure chamber 226, a negative pressure may be generated in the negative-pressure chamber 226. Generation of a negative-pressure in the negative-pressure chamber 226 may cause a pressure differential to arise across the diaphragm 224. If the pressure in the negative-pressure chamber 226 is lower than the pressure in the ambient chamber 238, the pressure differential may urge the diaphragm 224 away from the wall 244. If the diaphragm 224 is urged away from the wall 244, the boss 242 may disengage from the tube 240, uncompressing the tube 240 so that fluid may flow through the tube 240 from the fluid source 118 to the dressing 102. Venting of the negative-pressure chamber 226, such as through the negative-pressure source 104, may decrease the pressure differential across the diaphragm 224, allowing the spring 230 to move the diaphragm 224 back to the position of FIG. 7 so that the boss 242 engages the tube 240 to stop flow from the fluid source 118 to the dressing 102.

The systems, apparatuses, and methods described herein may provide significant advantages. Example embodiments of the cartridge have been described herein that can be combined with an existing negative-pressure wound treatment therapy system to provide controlled instillation therapy. The cartridge can also be calibrated to provide a dosage of fluid at a pressure suitable for use with a tissue site, for example, approximately 100 mmHg. The cartridge can also be calibrated to provide an accurate dosing of a prescribed amount of fluids. Furthermore, the cartridge can be used with a multi-channel negative-pressure system so that the multi-channel negative-pressure system can provide both instillation and negative-pressure therapy. Alternatively, multiple cartridges can be used with a multi-channel negative-pressure system to provide instillation of multiple different types of fluids. The cartridge may also be combined with a tissue site drain to allow for continuous washing of the tissue site with instillation fluids. Example embodiment may also include a negative-pressure therapy system having the capability to determine if a canister or an instillation cartridge is fluidly coupled to the negative-pressure source and provide an appropriate therapy in response to the determination.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for providing instillation therapy with a negative-pressure source, the apparatus comprising:
   a housing having an ambient chamber and a negative-pressure chamber fluidly isolated from each other;
   a moveable barrier disposed in the housing between the ambient chamber and the negative-pressure chamber;
   a tube configured to be fluidly coupled to a fluid source and a dressing, the tube passing through the ambient chamber;
   a negative-pressure inlet in fluid communication with the negative-pressure chamber; and a biasing element coupled to the moveable barrier and operable to selectively permit fluid flow through the tube in response to operation of the negative-pressure source.

2. The apparatus of claim 1, wherein the biasing element comprises a spring.

3. The apparatus of claim 1, wherein the moveable barrier comprises a diaphragm.

4. The apparatus of claim 1, further comprising a pinch valve coupled to the moveable barrier.

5. The apparatus of claim 4, wherein the biasing element is configured to bias the pinch valve to engage the tube.

6. The apparatus of claim 4, wherein the pinch valve comprises a triangularly shaped boss having an apex configured to engage the tube.

7. The apparatus of claim 1, wherein the biasing element permits fluid flow through the tube in response to a negative pressure supplied to the negative-pressure chamber.

* * * * *